(12) United States Patent
Wuerzburger et al.

(10) Patent No.: US 11,837,078 B2
(45) Date of Patent: Dec. 5, 2023

(54) AMBULATORY MEDICAL DEVICE WITH VIBRATOR

(71) Applicant: Roche Diabetes Care, Inc., Indianapolis, IN (US)

(72) Inventors: Steffan Wuerzburger, Worms (DE); Hans List, Oberzent (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 259 days.

(21) Appl. No.: 17/492,158

(22) Filed: Oct. 1, 2021

(65) Prior Publication Data

US 2022/0020251 A1   Jan. 20, 2022

Related U.S. Application Data

(63) Continuation of application No. PCT/EP2020/059096, filed on Mar. 31, 2020.

(30) Foreign Application Priority Data

Apr. 2, 2019 (EP) .................................... 19166776

(51) Int. Cl.
*G08B 6/00* (2006.01)
*A61M 5/14* (2006.01)
*A61M 5/142* (2006.01)

(52) U.S. Cl.
CPC .............. *G08B 6/00* (2013.01); *A61M 5/1413* (2013.01); *A61M 5/14248* (2013.01); *A61M 2205/582* (2013.01)

(58) Field of Classification Search
CPC ............ A61M 5/1413; A61M 5/14248; A61M 2205/582; A61M 2205/3693;
(Continued)

(56) References Cited

U.S. PATENT DOCUMENTS 6,126,595 A  10/2000 Amano et al.
6,126,596 A  10/2000 Freedman
(Continued)

FOREIGN PATENT DOCUMENTS

EP  2 422 830 A1  2/2012
EP  2 626 093 A1  8/2013
(Continued)

OTHER PUBLICATIONS

International Search Report and Written Opinion of the International Searching Authority, PCT/EP2020/059096, dated May 15, 2020, 10 pages.
(Continued)

*Primary Examiner* — Ojiako K Nwugo
(74) *Attorney, Agent, or Firm* — Bose McKinney & Evans LLP

(57) ABSTRACT

An ambulatory medical device for attachment to a person's body includes a housing having a wall and a vibrator coupler. A convex outer surface of the vibrator coupler projects from the wall towards the outside of the housing. The vibrator coupler is coupled to the wall via a connector arranged along the circumference of the vibrator coupler. A vibrator mechanically vibrates upon activation. The vibrator is arranged at least partially inside a volume defined by the vibrator coupler and is mounted to the vibrator coupler. A skin attachment device is also disclosed. It has a substantially planar body having a skin attachment side and an opposing medical device mounting side. The skin attachment side includes a skin attachment structure for releasably attaching the skin attachment device to a person's skin and the medical device mounting side includes a medical device mount for releasably engaging with the ambulatory medical device.

16 Claims, 2 Drawing Sheets

(58) Field of Classification Search
CPC .......... A61M 2205/58; A61M 5/16831; A61B 5/14532; A61B 5/7455; A61B 5/4839; G08B 6/00
See application file for complete search history.

(56) References Cited

U.S. PATENT DOCUMENTS

| | | | |
|---|---|---|---|
| 10,960,132 B1* | 3/2021 | Schleicher | A61M 5/31501 |
| 2008/0125700 A1 | 5/2008 | Moberg et al. | |
| 2010/0160855 A1* | 6/2010 | Bernini | A61M 5/14244 604/67 |
| 2012/0112903 A1* | 5/2012 | Kaib | A61B 5/02438 340/539.12 |
| 2013/0147490 A1* | 6/2013 | Lindegger | A61M 5/14244 324/435 |
| 2014/0200426 A1* | 7/2014 | Taub | A61B 5/14532 600/347 |
| 2014/0323961 A1* | 10/2014 | Blomquist | A61M 5/142 604/66 |
| 2015/0182695 A1* | 7/2015 | Rosinko | A61M 5/168 604/500 |
| 2015/0290390 A1 | 10/2015 | Ring et al. | |
| 2016/0038673 A1* | 2/2016 | Morales | G16H 50/50 700/282 |
| 2016/0045386 A1* | 2/2016 | Sandler | A61B 5/6811 623/24 |
| 2019/0167900 A1* | 6/2019 | Friedli | A61M 5/172 |
| 2020/0286612 A1* | 9/2020 | Mears | G16H 20/60 |

FOREIGN PATENT DOCUMENTS

| | | |
|---|---|---|
| WO | WO 2014/164018 A1 | 10/2014 |
| WO | WO 2018/029162 A1 | 2/2018 |

OTHER PUBLICATIONS

Extended European Search Report, EP 19 166 776.5, dated Aug. 7, 2019, 6 pages.

* cited by examiner

AMBULATORY MEDICAL DEVICE WITH VIBRATOR

RELATED APPLICATIONS

This application is a continuation of PCT/EP2020/059096, filed Mar. 31, 2020, which claims priority to EP 19 166 776.5, filed Apr. 2, 2019, the entire disclosures of both of which are hereby incorporated herein by reference.

BACKGROUND

This disclosure relates to ambulatory medical devices, to skin attachment devices for ambulatory medical devices, and to ambulatory medical systems. This disclosure further relates to methods for providing tactile indications carrying a medical device. The ambulatory medical device may in particular be an ambulatory infusion device.

Ambulatory medical devices are used in large numbers in a variety of applications. By way of example, ambulatory insulin pumps form the basis for therapy of diabetes mellitus by way of continuous subcutaneous insulin infusion (CSII). Also, in diabetes therapy, continuous glucose monitors (CGM's) are used in increasing numbers.

In addition to devices that are carried separate from the body, e.g., with a belt clip, in a trousers' pocket or as necklace, so-called patch devices are becoming more and more popular. Such patch devices are directly attached, typically adhesively attached, to the body for an application time.

Among other things, such ambulatory medical devices are, according to the state of the art, designed to withstand various adverse conditions, such as mechanical shocks or impact, and are further required to be hermetically sealed and in particular water tight.

For such devices, the provision of non-visual user indications to the user is critical due to the sealed housing. In particular, a vibration device in form of a vibrator motor is common for providing user indications in a well recognizable but discrete manner. The vibrator motors are of generally the same type as widely used for example in cell phones or pager devices. Normally the vibrator, in particular, vibrator motor is mounted on the inside of the housing in a substantially rigid way. For transmitting the vibration to the outside, the whole housing or at least a substantial part thereof needs to be excited to mechanically vibrate. Only a fraction of the acceleration that results from the vibration of the vibrator, however, is transferred to the housing structure. Consequently, the vibration that is sensed by the person carrying the device is low and in extreme cases nothing can be sensed at all. This is particularly critical for a number of persons, e.g., many diabetics, who suffer from reduced tactile sensitivity.

Further, if a vibration is transmitted from a vibrator to the housing as a whole, a skin-piercing element, such as an infusion cannula or a transcutaneous glucose sensing element, may also be caused to vibrate, resulting in discomfort and potentially severe pain. Further, in the case of an infusion cannula, the vibration may adversely affect the infusion, since the cannula channel in the skin is likely to be widened, resulting in a potential drug flow of infused drug out of the body along the outer side of the cannula.

U.S. Pat. No. 6,126,595 discloses a housing that has a locally reduced thickness of a housing wall in an area surrounding a piezo vibrator that is mounted to the housing wall. Due to the reduced wall thickness, the ability of the housing wall to be mechanically excited and move forth and backwards is somewhat improved.

SUMMARY

This disclosure improves the state of the art regarding the provision of tactile indications for an ambulatory medical device. Favorably, the drawbacks of the state of the art as mentioned above are at least partially avoided.

In an aspect, an ambulatory medical device is disclosed that is designed for attachment to a person's body. The ambulatory medical device includes a housing, the housing having a wall element (also referred to herein as "wall") and a vibrator coupling element (also referred to herein as "vibrator coupler"). The vibrator coupling element is hollow. A convex outer surface of the vibrator coupling element projects from the housing wall towards the outside of the housing. The vibrator coupling element is coupled to the wall element via a connection element (also referred to herein as "connector"), with the connection element being arranged along a circumference of the vibrator coupling element. The ambulatory medical device further includes a vibrator. The vibrator is configured to mechanically vibrate upon activation. The vibrator is arranged at least partially inside a volume defined by the vibrator coupling element and mounted to the vibrator coupling element. In some embodiments, the vibrator is completely or substantially completely arranged inside the volume of the vibrator coupling element.

The wall element, the vibrator coupling element and the connection element are typically structurally distinct. They may, however, be permanently or releasably connected.

The ambulatory medical device is skin-mountable by direct attachment to the skin, and/or via a skin attachment device as intermediate element as discussed in more detail further below.

The mounting of the vibrator to the vibrator coupling element is a rigid mounting, resulting in a stiff mechanical coupling. Consequently, a mechanical vibration of the vibrator is mainly and favorably substantially completely transferred to the vibrator coupling member. Typically, the vibrator is not mechanically coupled or attached to other parts of the medical device in a way that would limit or influence its freedom to move, in particular, to vibrate. The mounting of the vibrator to the vibrator coupling element may be achieved, for example, by gluing, clamping, or screwing. The electrical connection of the vibrator with further circuitry of the ambulatory medical device is favorably flexible and compensates for the relative movement of the vibrator relative to the further components of the medical device. The electrical connection may, for example, be flexible cables or a flexible printed circuited board (flexprint).

The housing may be of any desired shape, for example box- or disc-shaped. Further, the housing may have planar and/or non-planar walls. The wall element as mentioned before is substantially planar and faces, in use, towards the person's skin. Both the housing and the vibrator coupling element are typically made from plastics. The vibrator coupling element may in some embodiments be arranged in a vibrator coupling opening in form of a cutout or aperture of the wall element, with an edge of the aperture circumferentially surrounding the vibrator coupling element. Typically, but not necessarily, a footprint of the aperture and of the vibrator coupling element (transverse to the wall element) is circular. The aperture and the vibrator coupling element may have corresponding footprints. In some embodiments, the footprint of the aperture is somewhat larger as compared to the vibrator coupling element to enable displacement of the vibrator coupling element relative to the wall element.

The convex outer surface of the vibrator coupling element may be smooth. In alternative embodiments, the convex outer surface of the vibrator coupling element may be provided with a single or a plurality of additional burls or protrusions, in particular in an area that contacts the skin during application, thereby creating a non-smooth surface. Such a non-smooth surface favorably increases the tactile sensing of the vibrations by the user. Similarly, the outer surface of the vibrator coupling element may be roughened in particular in an area that contacts the skin during application.

Via the design described herein, the vibration transfer from the vibrator to the user's skin is improved, resulting in an improved vibration sensing. Further, disadvantageous vibration of a skin-piercing element such as an infusion cannula or transcutaneous glucose-sensor is reduced and may be eliminated. These advantages are caused by the fact that a vibration is largely or even fully limited to the vibrator coupling element, rather than the housing as a whole.

In some embodiments, the vibrator is configured to vibrate in a plane parallel to the wall element. In such embodiment, the vibration is accordingly tangential to the wall element. A vibration in a plane may be one dimensional (in a direction along one axis), or two-dimensional. In some alternative embodiments, the vibrator may be configured to vibrate in a direction transverse or perpendicular to the wall element and/or oblique to the wall element.

In some embodiments, the vibrator coupling element is calotte-shaped. In such embodiment, the convex side of the calotte, namely, the vibrator coupling element, projects from the wall element. Further, the vibrator is at least partly arranged inside the calotte, i.e., the vibrator coupling element. This type of embodiment is particularly favorable for transmitting the vibration to the user's skin. In use, an apex region of the calotte is favorably gently pressed into the skin without causing skin irritation. Further, the arrangement of the vibrator inside the calotte is favorable regarding an efficient space usage and the desired stiff coupling. The calotte may have the shape of a sphere or ellipsoid section. In alternative embodiments, the vibrator coupling element may have a different shape, for example, a generally cylindrical shape with a tubular side wall and planar skin-contacting bottom wall, or a tubular section that projects from the wall element and a calotte-shaped skin-contacting section.

In some embodiments, the vibrator coupling element is displaceable relative to the wall element. The vibrator coupling element may especially be displaceable in a direction that corresponds to, in particular, is parallel to a vibration direction of the vibrator. That is, in embodiments in which the vibrator is configured to vibrate in a plane parallel or tangential to the wall element, the vibrator coupling element may also be displaceable relative to the wall element in a plane parallel or tangential to the wall element. In embodiments in which the vibrator is configured to vibrate in a direction perpendicular to the wall element, the vibrator coupling element may also be displaceable relative to the wall element in a direction perpendicular to the wall element. The vibrator coupling element being displaceable in this way improves the vibration transfer from the vibrator to the skin. Favorably, the possible displacement of the vibrator coupling element is sufficiently large in order not to hinder the movement of the vibrator coupling element resulting from the vibration. A displacement of the vibrator coupling element is to be understood in the sense of a movement of the vibrator coupling element as a whole. A displaceable arrangement of the vibrator coupling element is particularly efficient in decoupling the vibrator coupling element from the wall element, thereby restoring the vibration to the vibrator coupling element. In alternative embodiments, the vibrator coupling element is configured to vibrate via small internal deformation, without being displaced, that is, moved as a whole.

In some embodiments, the connection element is flexible. A flexible connector is particularly favorable to enable displacement of the vibrator coupling element relative to the wall element and the housing as a whole as explained before.

The connection element may in some embodiments surround the vibrator coupling element, favorably over its full circumference. It may be attached to the vibrator coupling element along its outer circumference and to the wall element. In some embodiments, the footprint of the vibrator coupling element is normally somewhat smaller as compared to an aperture of the wall element in which the vibrator coupling element is arranged as explained before. In such embodiments, a transversal or radial gap accordingly exists between the wall element and the vibrator coupling element. This gap is bridged by the connection element. Further, in some embodiments, the vibrator coupling element is axially displaced with respect to the wall element, more particularly a plane defined by the wall element, resulting in an axial gap that is also bridged by the connection element. In this context, axial refers to a direction transverse to the wall element, while radial refers to a direction parallel to the wall element.

In some embodiments, the connection element is designed as bellows. The connection element may be made of any suited material of sufficient flexibility, for example rubber or silicone. The connection element may be a separate component that is connected to the wall element and the vibrator coupling element via corresponding mating structures, or may be formed integrally with the housing wall and/or the vibrator coupling element, for example by two-component injection molding.

In some embodiments, the connection element comprises at least one swage. Swages are a particularly favorable way for realizing a flexible coupling between wall element and vibrator coupling element. One or more swages may be present in functional sequential arrangement.

In some further embodiments, the connection element is an adhesive element via which the vibrator coupling element is adhesively attached to the wall element. In such embodiments, the connection element may be rigid or substantially rigid.

In some embodiments, the housing is substantially rigid. A generally rigid housing is favorable and may be necessary in order to withstand external forces that typically act on the ambulatory medical device in use and may, if not absorbed, damage the device and/or lead to critical malfunctions. A rigid housing, however, is disadvantageous for transmitting vibrations from inside the housing to the outside. In this context, this disclosure presents the particular advantage of ensuring, by means of the vibrator coupling element, a good vibration transmission even though the housing in general is stiff and rigid.

In some embodiments, the mass of the vibrator coupling element is small as compared to the mass of the housing. A small mass of the vibrator coupling element results in a large vibration amplitude and therefore good tactile sensing by the person carrying the device. Favorably, the mass of the vibrator coupling element is also small against the wall element.

In some embodiments, the wall element is coupled to the vibrator coupling element in a hermetically sealing manner. This may be achieved by a circumferentially closed connection element without openings. Such embodiment is particularly favorable in combination with a generally tight or hermetically sealed housing. The expression "sealed" refers to a protection against the passing of one or more of liquids, gas, steam, and particles, such as dust.

In some embodiments, the vibrator is a coin vibration motor. Generally, vibration motors are based on the rotation of an eccentric mass coupled to the motor shaft causing vibration due to the unbalanced mass. A coin vibration motor (also referred to as flat vibration motor or pancake vibration motor) has a particularly thin, coin-shaped motor. Such coin vibrator motor is favorably mounted with the motor axis being transverse to the plane of the wall element and may be favorably fully arranged within the, e.g., calotte-shaped vibrator coupling element.

In some further embodiments, the vibrator is an eccentric rotating mass vibration motor (ERM). For this type of design, an eccentric mass is mounted to the axis of a miniaturized electric motor of typical cylindrical shape.

In some further embodiment, the vibrator is a linear resonant actuator (LRA). Such LRAs are generally designed similar to a dynamic loudspeaker as known in the art, but are provided with a vibration mass instead of a membrane. Their overall shape may be coin-like as for a coin vibration motor. For a coin vibration motor, however, the vibration direction is parallel or tangential to the top and bottom surface of the coin-shaped housing. For an LRA, in contrast, it is transverse, or perpendicular.

Generally, the term "vibrator" is to be understood as an electrically actuated device that generates a mechanical vibration upon actuation. Vibrators within this meaning are also commonly used, e.g., in cell phones or pager devices.

In some embodiments, the ambulatory medical device is an ambulatory infusion device, in particular, an insulin pump. Such ambulatory infusion device as used, in particular in diabetes therapy via continuous subcutaneous insulin infusion (CSII) and is designed to administer a liquid drug, for example, a liquid insulin formulation, in small quantities substantially continuously typically according to a time-varying infusion schedule, and further administer larger drug amounts on demand. A variety of general designs for ambulatory infusion devices is known in the art. In alternative embodiments, the ambulatory medical device is or includes additionally or alternatively other types of therapeutic devices, such as a stimulation device, and/or is a diagnostic device, such as a continuous glucose monitor, as also used in diabetes therapy in increasing numbers. Typically, the ambulatory medical device is an electronic device and includes control circuitry as generally known in the art, based on, e.g., one or more microcomputers or microcontrollers.

In some embodiments, the housing includes an attachment device mounting structure for releasable mounting the ambulatory medical device to a skin attachment device. The attachment device mounting structure is typically designed for releasable positive locking and may be designed by one or more catches hooks or notches that are designed for engagement with complementary counter elements as explained further below.

According to a further aspect, the overall objective is achieved by a skin attachment device. The skin attachment device includes a substantially planar body with a skin attachment side and an opposing medical device mounting side. The skin attachment side includes a skin attachment structure for releasably attaching the skin attachment device to a person's skin. The medical device mounting side includes a medical device mounting structure for releasably engaging with the attachment device mounting structure of an ambulatory medical device as discussed before and/or further below. The body includes a vibrator coupling opening. The vibrator coupling opening, typically in the form of a cutout or aperture, is through-going and arranged to allow the projection of a vibrator coupling element as explained further below in more detail. A skin attachment device is frequently also referred to as "cradle."

The skin attachment structure is typically realized by way of an adhesive coating and/or layer that is initially covered by a removable liner. The medical device mounting structure may in particular be realized as one or more counter elements for the attachment device mounting structure of the ambulatory medical device. The attachment device mounting structure and the medical device mounting structure may, in combination, form a releasable snap fit connection. In other embodiments, the attachment device mounting structure and the medical device mounting structure may cooperate according to a different principle. For example, the attachment device mounting structure or the medical device mounting structure may be or have a magnet and the other may be or have a corresponding ferromagnetic element, thereby realizing a magnetic coupling.

The skin attachment device further includes a cannula coupling structure for coupling with a cannula and/or a fluidic coupling structure as explained further below in the context of exemplary embodiments. Typically, the cannula attachment structure is distinct from the vibrator coupling opening.

According to a further aspect, this disclosure provides an ambulatory medical system. The ambulatory medical system includes an ambulatory medical device and at least one skin attachment device. In a configuration in which the medical device is mounted to the skin attachment device, the vibrator coupling element projects through the vibrator coupling opening towards the skin attachment side.

Typically, the skin attachment device is designed for single use over a certain time-period of, e.g., a number of days or weeks and subsequent disposal, while the ambulatory medical device is designed for a longer usage time of, e.g., several months up to several years. Such ambulatory medical system allows to carry the ambulatory medical device in sequence with a number of skin attachment devices, with the skin-contacting skin attachment device being repeatedly replaced.

In such ambulatory medical system, the skin attachment device is, during application, arranged between the skin and the ambulatory medical device, with the wall element of the ambulatory medical device facing and contacting the medical device mounting side of the skin attachment device. Due to the vibrator coupling element projecting through the vibrator coupling opening, the distance between the wall element and the skin (as defined by the thickness of the body of the skin attachment device) is bridged, such that the vibrator coupling element directly contacts the skin. The vibrator coupling device projects beyond the plane that is defined by the skin attachment side.

In alternative embodiments of the ambulatory medical device, however, the ambulatory medical device is designed for direct skin attachment and may carry a skin attachment structure, e.g., an adhesive layer or coating, directly on the wall element that surrounds the vibrator coupling element.

According to a further aspect, this disclosure teaches a method for providing tactile indications to a person carrying an ambulatory medical device. The method includes actuating the vibrator motor and thereby transmitting a vibration to the person's skin in a plane parallel to the wall element.

Tactile indications may be provided as particularly discrete user feedback and/or alerting the person in case of exceptional situations that may require immediate attention, such as an empty battery, an empty drug reservoir or a malfunction, in addition or alternatively to visual and/or audio indications.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

In the following, exemplary embodiments are described in more detail with additional reference to the figures.

It shall be understood that terms such as "horizontal" and "vertical" are generally used herein to establish positions of individual components relative to one another rather than an absolute angular position in space. Further, regardless of the reference frame, in this disclosure terms such as "vertical," "parallel," "horizontal," "right angle," "rectangular" and the like are not used to connote exact mathematical orientations or geometries, unless explicitly stated, but are instead used as terms of approximation. With this understanding, the term "vertical," for example, certainly includes a structure that is positioned exactly 90 degrees from horizontal, but should generally be understood as meaning positioned up and down rather than side to side. Other terms used herein, such as top, bottom, left, right, above and below, are used to aid the reader's understanding of the position of various parts or subparts relative to one another. Other terms used herein to connote orientation, position or shape should be similarly interpreted. Further, it should be understood that various structural terms used throughout this disclosure and claims should not receive a singular interpretation unless it is made explicit herein. All terms appearing in this disclosure and claims should be interpreted to mean "one or more" or "at least one," unless it is made explicit that a singular interpretation is intended.

Figure 1:
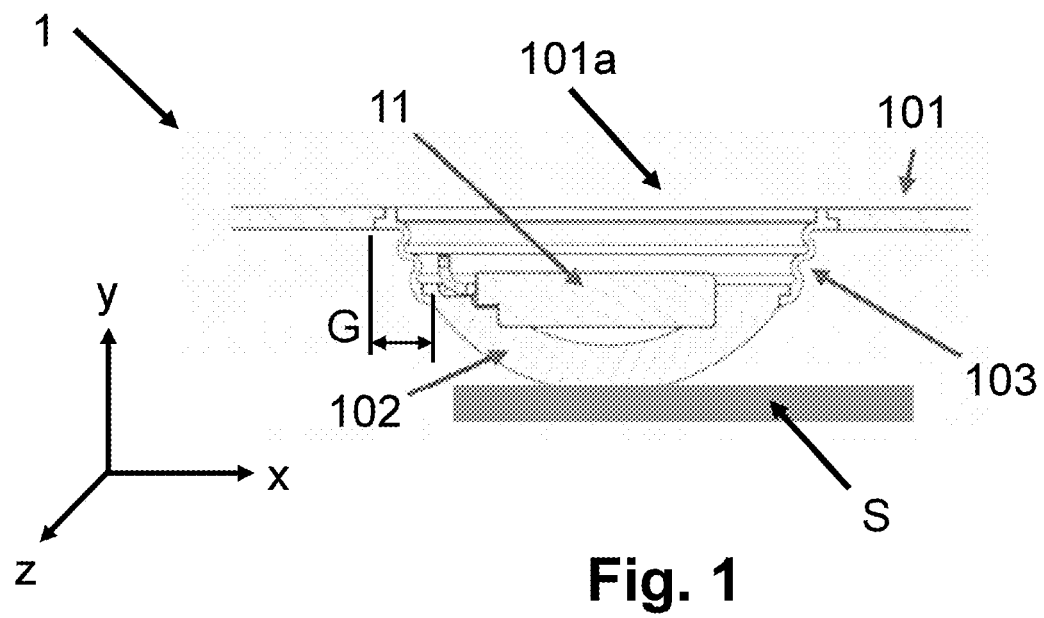
FIG. 1, shows part of an ambulatory medical device in a schematic side view.

FIG. 1 shows part of an ambulatory infusion device 1 in a schematic side view, the ambulatory infusion device 1 may in particular be an insulin pump and serves as exemplary ambulatory medical device. Alternatively, however, another type of ambulatory medical device, such as a continuous glucose monitor, may be present.

The ambulatory infusion device 1 comprises a housing 10 from which only a wall element ("wall") 101 is shown in FIG. 1 for clarity reasons. The wall element 101 is generally planar and may form the bottom of the favorably hermetically sealed housing 10. In application, the wall element 101 is parallel to and faces the skin S of a person carrying the ambulatory infusion device 1. The skin S and the wall element 101 are parallel to the x-z-plane. In a circular aperture 101a of the wall element 101, the vibrator coupling element in form of a calotte 102 is concentrically arranged such that the wall element 101 surrounds the vibrator-coupling element 102 when viewed in a direction along the y-axis. The housing 10 and in particular the wall element 101 as well as the calotte 102 are typically made from generally rigid plastics. Favorable, the calotte 102 has a small mass and in particular a mass that is small as compared to the total mass of the housing 10 and the wall element 101.

The ambulatory infusion device 1 is designed for skin attachment via a skin attachment device that bridges, in application, the distance between the housing 10, particularly the wall element 101 and the skin S. In FIG. 1, the skin attachment device is not shown for clarity reasons.

A vibrator in the form of coin vibrator motor 11 is rigidly mounted inside the calotte 102. The coin vibrator motor 11 is electrically connected with further circuitry of the ambulatory infusion device 1, for example a printed circuit board, via flexible wiring.

The diameter of the calotte 102 is somewhat smaller as compared to the diameter of the aperture 101a, resulting in a radial gap G between them. Further in this example, the calotte 102 is somewhat axially spaced apart from the wall element 101 towards the skin (in −y-direction). Between the aperture 101a and the calotte 102, a connection element in form of a bellows 103 is arranged that bridges the radial gap G and the axial distance between the calotte 102 and the wall element 101. The bellows 103 is made from resilient, respectively flexible material and is connected to the wall element 101 at the circumference of the aperture 101 as well as to the outer periphery of the calotte 102. The bellows 103 is ring-shaped in a viewing direction parallel to the y-axis and surrounds the calotte 102 over its whole periphery. As can be seen, the bellows 103 is provided with exemplary two swages that improve flexibility in particular in the x-z-plane. The bellows 103 provides an elastic mechanically elastic coupling between the wall element 101 and the calotte 102.

When actuated, the coin vibrator motor 11 vibrates parallel to the x-z-plane and the housing wall 101. Due to the rigid coupling of the coin vibrator motor 11 to the calotte 102 and the flexible coupling of the calotte 102 to the wall element 101 (via the bellows 103), the calotte 102 will also vibrate parallel to the x-z-plane with a significant amplitude that is well recognizable by the person carrying the device due to the calotte 102 contacting, in the region of its apex, the person's skin S.

Figure 2:
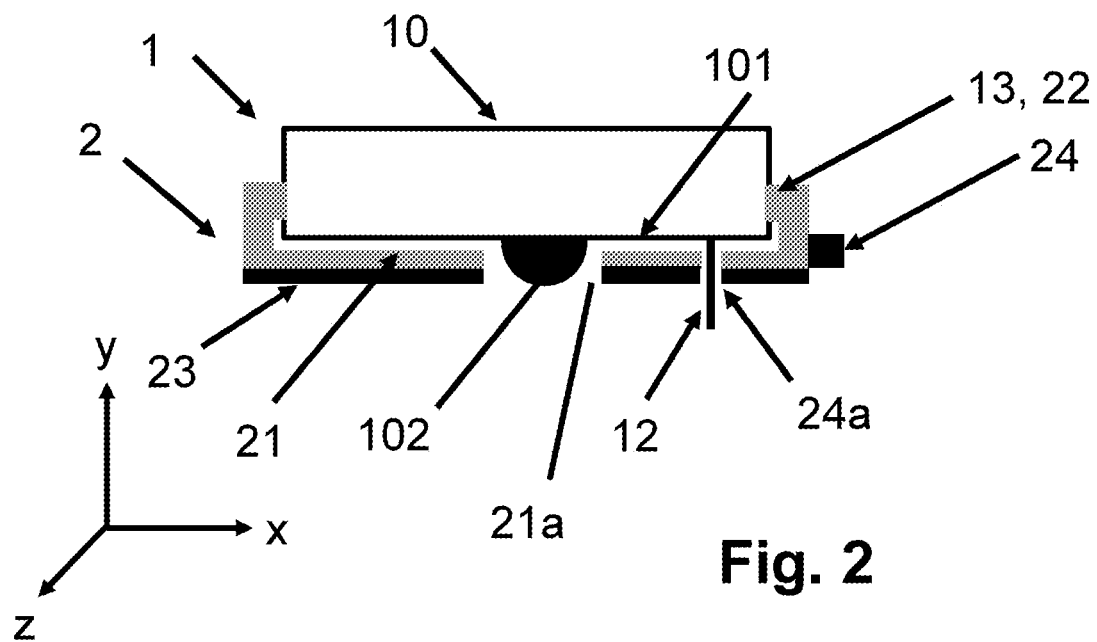
FIG. 2 shows an ambulatory medical system in a schematic side view.

In the following, reference is additionally made to FIG. 2. FIG. 2 schematically shows an ambulatory infusion device 1 of generally the same type as described before in the context of FIG. 1, together with a skin attachment device 2, thereby forming an ambulatory medical system.

The skin attachment device 2 comprises a generally plate-shaped body 21. At a skin-attachment side (bottom side in FIG. 2), a generally continuous adhesive layer 23 is foreseen for releasable skin attachment. At the opposing medical device mounting side (top side in FIG. 2), the plate-shaped body 21 comprises a medical device mounting structure 22 for releasable engaging with a corresponding attachment device mounting structure (not shown in detail) of the ambulatory infusion device 1 by way of releasable positive locking. In a coupled state, the ambulatory infusion device 1 and the skin attachment device 2 form a sandwich structure. The body 21 has a vibrator coupling opening in the form of a through-going vibrator coupling aperture 21a that is, in a coupled state of ambulatory infusion device 1 and skin attachment device 2, aligned with the calotte 102 as vibrator coupling element. The calotte 102 projects through the vibrator coupling aperture 21a such that it slightly projects below the bottom side of the body 21 and the adhesive layer 23, thereby allowing its apex region to safely contact the person's skin. In order not to hinder the movement of the calotte 21, the diameter of the vibrator coupling aperture 21a is somewhat larger than the diameter respectively than the lateral dimensions of the calotte 102.

Furthermore, the skin attachment device 2 includes a cannula coupling structure that is realized by a through-going cannula aperture (not referenced) in the body 21, similar to the vibrator coupling aperture 21a and engagement means (not shown in detail) for a cannula 12. In a coupled state, the cannula 12 establishes a fluidic connection with the ambulatory infusion device 21, e.g., via a septum that is arranged in the wall element 101. Alternatively, or additionally, the skin attachment device 2 includes a fluidic coupling structure 24 in form of a fluid path that may, e.g., be integrated into the body 23 and a fluidic connector that is arranged at a periphery of the body 21 for coupling with a fluid line, e.g., a catheter. In such embodiments, the skin attachment device 2 may include a cannula to pierce a septum of the ambulatory infusion device as explained before. In a variant, the skin attachment device directly includes a cannula as integral part.

Figure 3:
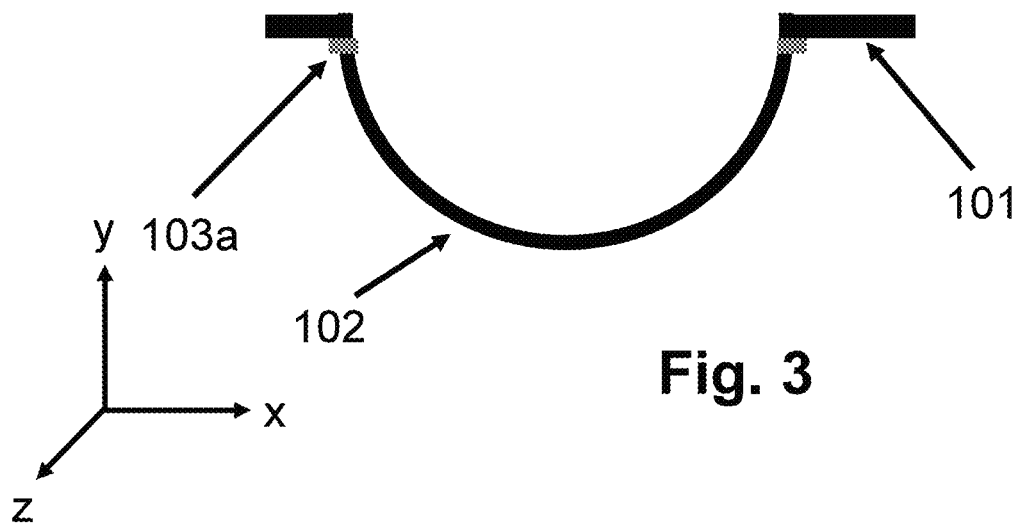
FIG. 3 schematically shows a further embodiment with a different attachment of the vibrator coupling element to the wall element.

FIG. 3 schematically shows a further embodiment with an alternative coupling of calotte 102 and wall element 101. In this embodiment, the connection element is not designed as bellows as in the before-described embodiments, but as adhesive element 103a in form of a ring-shaped adhesive layer at the interconnection of wall element 101 and calotte 102. This type of embodiment is particularly useful if the vibrator 11 (not shown) that is arranged inside the calotte 102 vibrates in the y-direction. This may be the case, for example, for an LRA as explained before.

Figure 4:
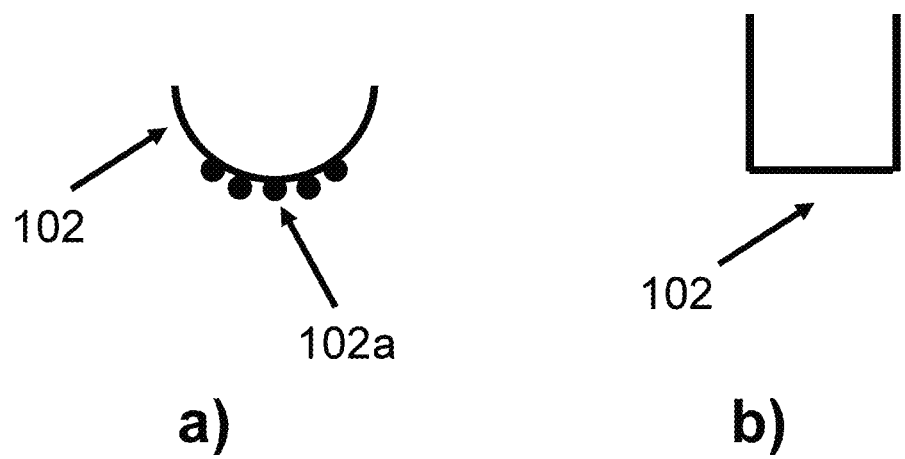
FIG. 4 schematically shows two alternative embodiments of the vibrator coupling element.

FIG. 4 shows further alternative designs for the vibrator coupling element 102 in a schematically manner. In FIG. 4a, the vibrator coupling element 102 is generally calotte-shaped as in the before-described embodiments. In an area that contacts the user's skin during application, however, a number of burls 102a is provided that improve the tactile sensing. In the embodiment of FIG. 4b, the shape of the vibrator coupling element 102 is generally cylindrical. If desired, burls 102a as shown in FIG. 4a may also be present.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE SIGNS 1 ambulatory medical device/ambulatory infusion device
10 housing
101 wall element
101a aperture
102 vibrator coupling element/calotte
102a burls
103 connection element/bellows
103a connection element/adhesive element
11 vibrator/coin vibrator motor
12 cannula
13 attachment device mounting structure
2 skin attachment device
21 body
21a vibrator coupling opening
22 medical device mounting structure
23 skin attachment structure/adhesive layer
24a cannula coupling structure
24 fluidic coupling structure
G gap
S skin

What is claimed is:

1. An ambulatory medical device for attachment to a person's body, the ambulatory medical device comprising:
   a) a housing having a wall and a vibrator coupler, wherein a convex outer surface of the vibrator coupler projects from the wall towards the outside of the housing, and the vibrator coupler is coupled to the wall via a connector that is arranged along a circumference of the vibrator coupler; and
   b) a vibrator configured to mechanically vibrate upon activation, wherein the vibrator is arranged at least partially inside a volume defined by the vibrator coupler and is mounted to the vibrator coupler.

2. The ambulatory medical device according to claim 1, wherein the vibrator is configured to vibrate in a plane parallel to the wall.

3. The ambulatory medical device according to claim 1, wherein the vibrator coupler is calotte-shaped.

4. The ambulatory medical device according to claim 1, wherein the vibrator coupler is displaceable relative to the wall.

5. The ambulatory medical device according to claim 1, wherein the connector is flexible.

6. The ambulatory medical device according to claim 1, wherein the connector comprises a bellows.

7. The ambulatory infusion device according to claim 1, wherein the housing is substantially rigid.

8. The ambulatory medical device according to claim 1, wherein the vibrator coupler has a smaller mass than the housing.

9. The ambulatory medical device according to claim 1, wherein the wall is coupled to the vibrator coupler in a hermetically sealed manner.

10. The ambulatory medical device according to claim 1, wherein the vibrator is a coin vibration motor.

11. The ambulatory medical device according to claim 1, wherein the ambulatory medical device comprises an insulin pump.

12. The ambulatory medical device according to claim 1, wherein the housing includes an attachment device mount for releasably mounting the ambulatory medical device to a skin attachment device.

13. A method for providing tactile indications to a person carrying an ambulatory medical device according to claim 1, the method including actuating the vibrator and thereby transmitting a vibration in a plane parallel to the wall.

14. A skin attachment device, comprising:
   a substantially planar body having a skin attachment side and an opposing medical device mounting side, wherein the skin attachment side includes a skin attachment structure for releasably attaching the skin attachment device to a person's skin and the medical device mounting side includes a medical device mount for releasably engaging with the attachment device mount of an ambulatory medical device including:
a) a housing having a wall and a vibrator coupler, wherein a convex outer surface of the vibrator coupler projects from the wall towards the outside of the housing, and the vibrator coupler is coupled to the wall via a connector that is arranged along a circumference of the vibrator coupler, wherein the housing further includes the attachment device mount for releasably mounting the ambulatory medical device to the skin attachment device; and
b) a vibrator configured to mechanically vibrate upon activation, wherein the vibrator is arranged at least partially inside a volume defined by the vibrator coupler and is mounted to the vibrator coupler;
wherein the body includes a vibrator coupling opening and the skin attachment device further includes a cannula coupler for coupling with a cannula and/or a fluidic coupling structure.

15. An ambulatory medical device for attachment to a person's body, the ambulatory medical device comprising:

a housing having a wall and a vibrator coupler, wherein a convex outer surface of the vibrator coupler projects from the wall towards the outside of the housing, and the vibrator coupler is coupled to the wall via a connector that is arranged along a circumference of the vibrator coupler, wherein the housing further includes an attachment device mount for releasably mounting the ambulatory medical device to the skin attachment device;
a vibrator configured to mechanically vibrate upon activation, wherein the vibrator is arranged at least partially inside a volume defined by the vibrator coupler and is mounted to the vibrator coupler; and
a skin attachment device according to claim 14, wherein, in a configuration in which the medical device is mounted to the skin attachment device, the vibrator coupler projects through the vibrator coupling opening towards the skin attachment side.

16. A method for providing tactile indications to a person carrying an ambulatory medical device according to claim 15, the method including actuating the vibrator and thereby transmitting a vibration in a plane parallel to the wall.

* * * * *